(12) United States Patent
Wongosari et al.

(10) Patent No.: US 7,278,589 B2
(45) Date of Patent: Oct. 9, 2007

(54) OPEN GEL DELIVERY DEVICE

(75) Inventors: Anita Wongosari, San Luis Obispo, CA (US); Padma Prabodh Varanasi, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 256 days.

(21) Appl. No.: 10/712,457

(22) Filed: Nov. 13, 2003

(65) Prior Publication Data

US 2004/0126271 A1 Jul. 1, 2004

Related U.S. Application Data

(60) Provisional application No. 60/426,588, filed on Nov. 15, 2002.

(51) Int. Cl.
*A24F 25/00* (2006.01)

(52) U.S. Cl. .............................. 239/60; 239/34; 239/57; 424/76.4

(58) Field of Classification Search ................. 239/34, 239/57, 53, 55, 60; 424/76.3, 76.4
See application file for complete search history.

(56) References Cited

U.S. PATENT DOCUMENTS

| 3,730,434 | A | * | 5/1973 | Engel | 239/47 |
| 3,910,495 | A | * | 10/1975 | Cummings et al. | 239/58 |
| 4,157,787 | A | * | 6/1979 | Schwartz | 239/56 |
| 4,809,912 | A | * | 3/1989 | Santini | 239/57 |
| 5,060,858 | A | * | 10/1991 | Santini | 239/57 |
| 5,422,078 | A | * | 6/1995 | Colon | 422/123 |
| 5,746,019 | A | * | 5/1998 | Fisher | 43/1 |
| 6,039,266 | A | * | 3/2000 | Santini | 239/60 |

FOREIGN PATENT DOCUMENTS

| EP | 1177799 A1 | * | 2/2002 |
| GB | 2260494 A | | 4/1993 |
| WO | WO 00/24434 | | 5/2000 |

* cited by examiner

*Primary Examiner*—Steven J. Ganey

(57) ABSTRACT

An open gel system for delivery of an active volatile possesses dimensions in the x, y, and z directions such as to release actives at an essentially constant rate from initiation of volatilization until completion of volatilization.

3 Claims, 2 Drawing Sheets

OPEN GEL DELIVERY DEVICE

RELATED APPLICATION

This application claims the benefit of U. S. Provisional Application No. 60/426,588, filed Nov. 15, 2002.

BACKGROUND OF THE INVENTION

The present invention relates to dispensers of volatile materials, which comprise a gel-type solid or semi-solid mass of material which is designed to release the maximum amount of volatile material over time, with a near-linear release rate. That is, the rate of release of volatile material is essentially uniform over the life of the dispenser.

The public is familiar with a number of solid or gel type air fresheners or dispensers of volatile materials. Most familiar are those which are sold to the public as Glade® air fresheners, produced by S. C. Johnson & Son, Inc., Racine, Wis., and Renuzit® air fresheners, a product of Dial Corporation, of Scottsdale, Ariz. While other dispensers of volatile materials, and air fresheners, are known, such as liquids incorporating wicks to assist in the evaporation of the liquid, and materials which may be heated to volatilize fragrances or other vaporizable components, the present invention is specifically directed to dispensers of volatile materials wherein a fragrance or other volatile active is encompassed within a solid or semi-solid material and is released over time by vaporization, to provide a pleasing fragrance, to release a pesticide or insect control material, to counter offensive odors, or to serve some other purpose. Aside from the problem of evaporation of volatile material from the dispenser prior to sale to the consumer, a problem associated with such dispensers is the drying, or shriveling, of the gel as the active material is released, resulting in an unattractive mass of hardened and emptied material to be disposed of, while the active, or volatile material is dispensed from the gel at an uneven or variable rate. That is, the fragrance or other active material is dispensed from the gel at a high rate upon initial exposure to the atmosphere, and more slowly as time passes, so that near the end of the life span of the dispensing device and its contained material, the volatile material is being released at rate which is much lower than the initial rate of release.

BRIEF SUMMARY OF THE INVENTION

We have found that a near-linear release of actives from a gel type dispenser of active materials may be achieved by providing the gel in a specific configuration, whereby delivery of the active to the atmosphere is enhanced.

Such systems may be classified, generally, as either a semi-enclosed gel, or an open gel system. For understanding, we have defined a semi-enclosed gel system as being one in which only part of the gel surface is exposed directly to flowing ambient air, and an open gel system as being one in which essentially the total available gel surface is exposed to the ambient air. The present invention addresses open gel systems.

The total release rate from an open gel ($TRR_{OG}$) is proportional to the surface area of the entire gel, as given by the following expression:

$$TRR_{OG}=K*C_o*A_D \quad (1)$$

Where, $C_o$=Concentration of the active at the gel surface,
K=Mass Transfer Coefficient, and
$A_D$=Surface Area of the gel in a the completely open device Based on Equation 1, a close to zero-order release (i.e., constant release rate with time) can be obtained in a completely open gel system only if the surface area of the gel $A_D$ remains constant or is permitted to change only by a small fraction during the entire life of the product. Thus, by careful control of the configuration of the gel surface we are able to achieve a zero-order release of active materials from the gel system, providing a relatively constant release rate of the active material from initial opening until final disposal upon completion of evaporation of the active material.

DETAILED DESCRIPTION OF THE INVENTION

Figure 1:
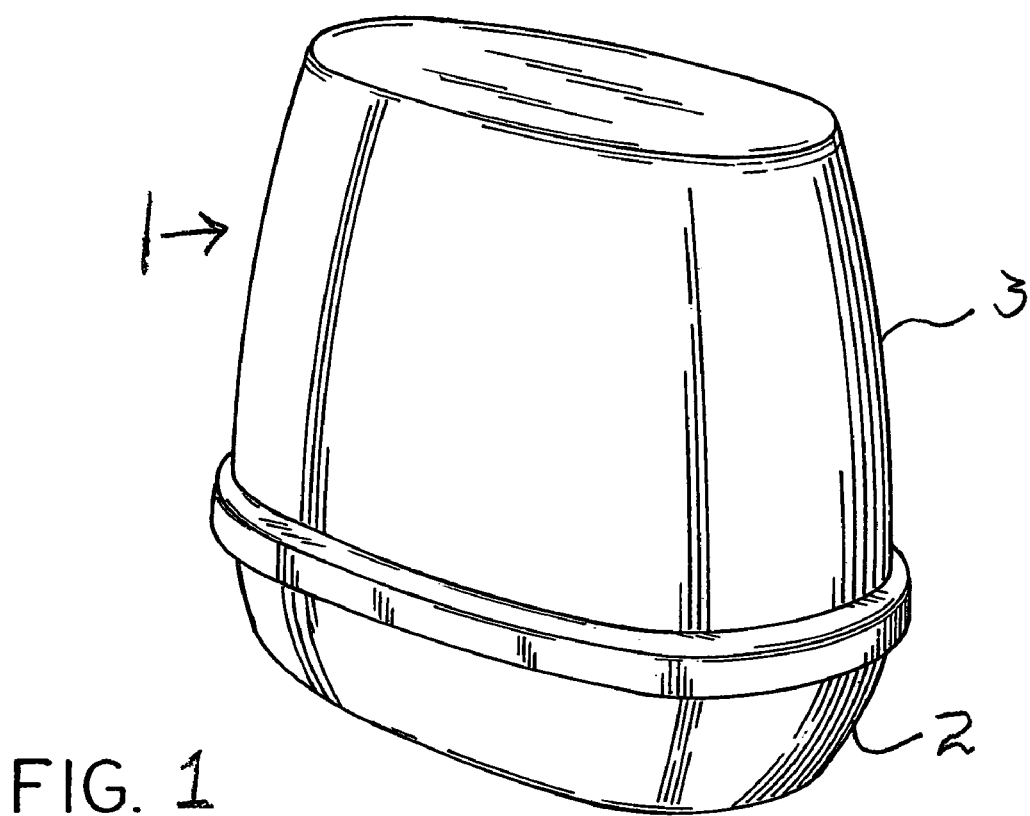
FIG. 1 illustrates the exterior container of a gel type dispenser of volatile materials in accordance with the present invention, in perspective view.

The present invention is related to gel type dispensers of active, or volatile materials, of the type commonly employed for air freshening, insect control, odor abatement, and the like. As shown in FIG. 1, such a dispenser (1), commonly comprises a base (2), and a cover or closure member (3) in which the base contains a volatile material, for example an air freshening deodorizer or fragrance, and in which the closure or cover is manually displaceable with respect to the base to provide means for control of the effective rate of volatilization or evaporation of the active material. In the case of an open gel system, the cover, 2, is simply removed from over the gel system, thereby permitting full access of the atmosphere to all available surfaces thereof. Such cover or closure member commonly may be positively locked with respect to the base, as shown in FIG. 1, to prevent unintended evaporation or volatilization of the active material. After opening of the closure member to expose the contained gel, the cover may be adjusted relative to the base to permit substantial control or variation of the rate of volatilization of the gel, in the case of a semi-enclosed gel system. Said base and cover may preferably be of a molded plastic material, although other materials may be utilized. The container may further comprise support members or posts, around which the gel member is molded or formed, which members or posts, which may be singular or plural, provide support and strength to the gel material in the container. The gel materials to which the present invention applies are well known to practitioners of the art, as are the methods of manufacture and positioning in a container such as shown in FIG. 1, and need not be discussed in greater detail for the purpose of this invention. The provision of active or volatile materials, and the choice thereof for the purposes of the dispensing devices of this invention, are also well known, and as such need not be discussed further. Rather, the present invention is directed to the relationship of the dimensions of the gel or solid actives containing material of the device.

Figure 2:
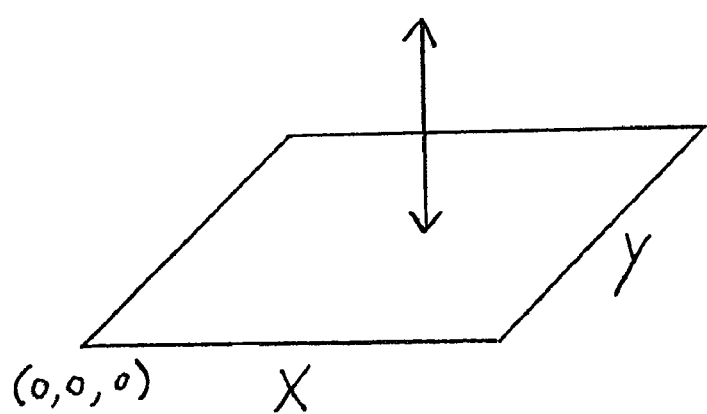
FIG. 2 illustrates the planar relationship of the coordinates of a gel system in accordance with the present invention.
Figure 3:
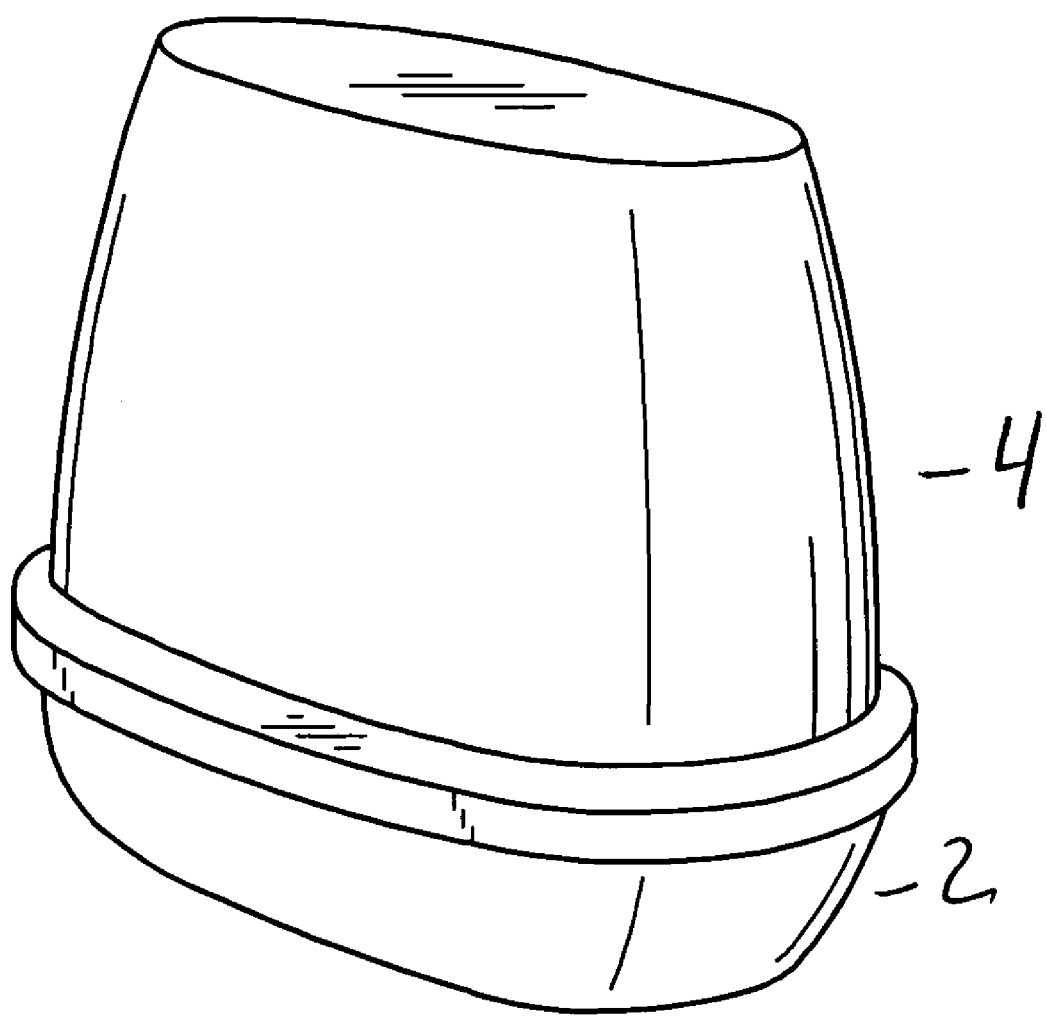
FIG. 3 depicts the FIG. 1 construction, but with a cover removed so as to show a gel 4.

To achieve a constant (zero-order) release rate for the volatile within a gel system, it is useful to consider that the three dimensional configuration of the actives containing material (hereinafter the gel system), as shown in FIG. 2.

In FIG. 2, dimensions x, y, and z are illustrated, having an origin point (0,0,0) at the intersection of said dimensions, wherein the gel system should be placed in such a way that it completely lies in the first quadrant of the x,y,z coordinate system and one point touches the origin point (0,0,0). The dimensions x, y, and z are defined as:

x=the dimension measured in the x direction of the projection of the gel system in the x-z plane
y=the dimension measured in the y direction of the projection of the gel system in the x-y plane
z=the dimension measured in the z direction of the projection of the gel system in the x-z plane The values of dimensions x, y, z are arranged in decreasing order such that:

$a_i^o$ is the largest value of x, y, or z at the initial condition,
$c_i^o$ is the smallest value of x, y, or z at the initial condition,
$b_i^o$ is the remaining value of x, y, or z at the initial condition,
$a_F^o$ is the largest value of x, y, or z at the final condition,
$c_F^o$ is the smallest value of x, y, or z at the final condition, and
$b_F^o$ is the remaining value of x, y, or z at the final condition, wherein initial condition and final condition refer to the dimensions of the gel system prior to volatilization, and after volatilization, respectively.

To maintain a release rate that does not deviate significantly from zero Order release, the following conditions must be met:

$b_i^o > 1.2\ c_i^o$, preferably $b_i^o > 5\ c_i^o$, and more preferably $b_i^o > 20\ c_i^o$, $a_i^o > 1.6\ c_i^o$, preferably $a_i^o > 8\ c_i^o$, and more preferably $a_i^o > 25\ c_i^o$, the value of $\alpha_i > 2.5$, preferably >10, and more preferably >30 where, $\alpha_i = (\alpha_1)(\alpha_2)(\alpha_3)$, wherein
$\alpha_1 = a_i^o/b_i^o$, $\alpha_2 = b_i^o/c_i^o$, and $\alpha_3 = a_i^o/c_i^o$ and, the value of $\beta_F/\alpha_i > 3$, preferably >10, and more preferably >30 where $\beta_F = (\beta_1)(\beta_2)(\beta_3)$, wherein
$\beta_1 = a_F^o/b_F^o$, $\beta_2 = b_F^o/c_F^o$, and $\beta_3 = a_F^o/c_F^o$ In accordance with these conditions, we have found that an open gel system having x, y, and z values of 9, 5, and 7, respectively, provide a relatively constant rate of dispensing the volatile material, such that the release rate of active materials is essentially the same from the initial activation of the dispenser until it is totally used up.

The invention claimed is:

1. An open gel delivery system in which an essentially constant release rate of active volatiles from the overall delivery system results from producing the gel system so as to provide that:

$b_i^O > 1.2 C_i^O$,
$a_i^O > 1.6 C_i^O$,
the value of $\alpha_i > 2.5$,
where, $\alpha_i = (\alpha_1)(\alpha_2)(\alpha_3)$, wherein
$\alpha_1 = a_i^O/b_i^O$, $\alpha_2 = b_i^O/c_i^O$, and $\alpha_3 = a_i^O/c_i^O$ and the value of $\beta_F/\alpha_1 > 3$,
where $\beta_F = (\beta_1)(\beta_2)(\beta_3)$, wherein
$\beta_1 = a_F^O/b_F^O$, $\beta_2 = b_F^O/c_F^O$, and $\beta_3 = a_F^O/c_F^O$, wherein
$a_i^O$ is the largest value of x, y, or z at the initial condition,
$c_i^O$ is the smallest value of x, y, or z at the initial condition,
$b_1^O$ is the remaining value of x, y, or z at the initial condition,
$a_F^O$ is the largest value of x, y, or z at the final condition,
$c_F^O$ is the smallest value of x, y, or z at the final condition, and
$b_F^O$ is the remaining value of x, y, or z at the final condition, wherein initial condition and final condition refer to different dimensions of the gel system prior to volatilization, and after volatilization, respectively, and x=the dimension measured in the x direction of the projection of the gel system in the x-z plane;
y=the dimension measured in the y direction of the projection of the gel system in the x-y plane; and
z=the dimension measured in the z direction of the projection of the gel system in the x-z plane.

2. The open gel delivery system of claim 1, wherein said active volatiles are selected from the group consisting of materials employed for air freshening, insect control, and odor abatement.

3. The open gel delivery system of claim 1, wherein said active volatile is a fragrance.

* * * * *